(12) United States Patent
Heitz et al.

(10) Patent No.: US 9,151,731 B2
(45) Date of Patent: Oct. 6, 2015

(54) FLUID PRESSURE CONTROL DEVICE FOR AN ANALYZER

(71) Applicant: IDEXX Laboratories Inc., Westbrook, ME (US)

(72) Inventors: Bernhard Heitz, Woodstock, GA (US); Kevin Kirspel, Cumming, GA (US)

(73) Assignee: IDEXX Laboratories Inc., Westbrook, ME (US)

( * ) Notice: Subject to any disclaimer, the term of this patent is extended or adjusted under 35 U.S.C. 154(b) by 399 days.

(21) Appl. No.: 13/744,458

(22) Filed: Jan. 18, 2013

(65) Prior Publication Data

US 2013/0186475 A1 Jul. 25, 2013

Related U.S. Application Data

(60) Provisional application No. 61/588,416, filed on Jan. 19, 2012.

(51) Int. Cl.
*F16K 31/02* (2006.01)
*G01N 27/416* (2006.01)
*G01N 33/00* (2006.01)
*G01N 33/49* (2006.01)

(52) U.S. Cl.
CPC ........ *G01N 27/4163* (2013.01); *G01N 33/0006* (2013.01); *G01N 33/4925* (2013.01); *Y10T 137/0396* (2015.04); *Y10T 137/7793* (2015.04)

(58) Field of Classification Search
CPC .......... G01N 27/4163; G01N 33/0006; G01N 33/4925; G05D 16/2013; G05D 16/2033; G05D 16/208; Y10T 477/60; Y10T 477/6197; Y10T 477/6243; Y10T 137/7759; Y10T 137/7761; Y10T 137/87917

USPC .................. 137/487.5, 487, 486, 12, 14, 613; 250/252.1; 422/112

See application file for complete search history.

(56) References Cited

U.S. PATENT DOCUMENTS

| | | | | |
|---|---|---|---|---|
| 4,373,549 | A * | 2/1983 | Nalepa et al. | 137/487.5 |
| 4,394,871 | A * | 7/1983 | Czajka et al. | 137/115.25 |
| 4,905,497 | A * | 3/1990 | Shindo et al. | 73/1.03 |
| 5,061,631 | A * | 10/1991 | Calabrese | 436/11 |
| 5,357,953 | A * | 10/1994 | Merrick et al. | 600/331 |
| 5,443,087 | A | 8/1995 | Myles | |
| 5,555,005 | A | 9/1996 | Pagnon | |
| 5,954,089 | A * | 9/1999 | Seymour | 137/487.5 |
| 6,003,543 | A * | 12/1999 | Sulatisky et al. | 137/487.5 |
| 6,568,416 | B2 | 5/2003 | Tucker et al. | |
| 6,581,623 | B1 * | 6/2003 | Carpenter et al. | 137/113 |
| 6,591,851 | B1 * | 7/2003 | Palten et al. | 137/12 |
| 6,648,021 | B2 | 11/2003 | Zheng et al. | |
| 6,857,447 | B2 * | 2/2005 | Olander et al. | 137/240 |
| 6,997,347 | B2 * | 2/2006 | Peng et al. | 222/3 |
| 7,083,487 | B2 * | 8/2006 | Weinel | 441/88 |

(Continued)

*Primary Examiner* — Craig Schneider
*Assistant Examiner* — Minh Le
(74) *Attorney, Agent, or Firm* — Carter, DeLuca, Farrell & Schmidt, LLP

(57) ABSTRACT

A fluid pressure control device, including a pressurized fluid inlet, a first valve in fluid communication with the pressurized fluid inlet and controlling the flow of fluid from the pressurized fluid inlet, a first pressure measurement device detecting a fluid pressure downstream of the first valve, and a controller electrically coupled to the first valve. The first pressure measurement device causes the controller to operate the first valve such that a fluid downstream of the first valve is maintained at a substantially constant pressure.

26 Claims, 6 Drawing Sheets

(56) References Cited

U.S. PATENT DOCUMENTS

| | | | |
|---|---|---|---|
| 7,258,132 B2 * | 8/2007 | Henderson et al. | 137/487.5 |
| 7,680,534 B2 | 3/2010 | Hopper et al. | |
| 7,823,436 B2 | 11/2010 | Monkowski et al. | |
| 2003/0183279 A1 * | 10/2003 | Chang | 137/487.5 |
| 2003/0213520 A1 * | 11/2003 | Prinz et al. | 137/487.5 |
| 2004/0238040 A1 * | 12/2004 | Furukawa | 137/487.5 |
| 2004/0244837 A1 * | 12/2004 | Nawata et al. | 137/487.5 |
| 2005/0189018 A1 * | 9/2005 | Brodeur et al. | 137/487.5 |
| 2005/0279408 A1 * | 12/2005 | Henderson et al. | 137/487.5 |
| 2007/0186982 A1 * | 8/2007 | Cohen et al. | 137/487.5 |
| 2008/0047607 A1 * | 2/2008 | Horsky et al. | 137/8 |
| 2011/0108126 A1 * | 5/2011 | Monkowski et al. | 137/12 |
| 2012/0103063 A1 * | 5/2012 | Bushey et al. | 73/23.41 |
| 2012/0132291 A1 * | 5/2012 | Monkowski et al. | 137/14 |
| 2013/0000742 A1 * | 1/2013 | Maier et al. | 137/14 |
| 2013/0115540 A1 * | 5/2013 | Falta et al. | 429/444 |

* cited by examiner

FLUID PRESSURE CONTROL DEVICE FOR AN ANALYZER

CROSS-REFERENCE TO RELATED APPLICATION

The present application claims the benefit of, and priority to, U.S. Provisional Patent Application No. 61/588,416, filed on Jan. 19, 2012, the entire disclosure of which is incorporated by reference herein.

BACKGROUND

1. Technical Field

The present disclosure is directed to a fluid pressure control device. More particularly, the present disclosure is directed to a system and method for supplying gas at a substantially constant pressure to calibrate a chemical analyzer, such as a blood gas analyzer.

2. Background of Related Art

Chemical analyzers measure a wide range of parameters in various fluids, for example, blood components. In order to calibrate some chemical analyzers, a pressurized fluid canister is provided to supply pressurized gases to the chemical analyzer in incremental measurement cycles. Calibration gases are typically a mixture of Nitrogen ($N_2$), Oxygen ($O_2$), and Carbon dioxide ($CO_2$). One type of chemical analyzer device, available from OPTI Medical Systems, employs a single-use cassette containing elements required for calibration of the chemical analyzer device. As heat is applied to the cassette, a calibration gas mixture is passed across the device sensors.

In many gas calibration systems used in chemical analysis, the pressure of the gas flowing from the pressurized fluid canister is governed by a mechanical pressure regulator. The regulator ensures that gas is supplied to the device within a desired pressure range. Other gas calibration systems employed in chemical analyzers maintain sensor integrity of the analyzer by using refrigerated storage of the sensors themselves, or employ liquid mixing systems to ensure proper operation. However, as can be imagined, the addition of refrigeration systems and/or liquid mixing features increases the complexity of such systems and provides additional sources of error or failure in the use of such systems. Further, gas calibration systems that employ liquid mixing or refrigeration require a steady supply chain of refrigerants, and a demanding maintenance cycle.

One concern associated with current systems to calibrate, for example, a blood gas analyzer, surrounds the relative high pressure of the canister of fluid. Canisters of fluid pressurized in excess of 30 psi are typically classified as hazardous goods for air transportation purposes, and thus are subject to high shipping costs. Similarly, canisters of fluid pressurized in excess of 60 psi are often categorized as hazardous goods for ground transportation. Thus, for many current canisters of fluid, the associated shipping costs can approach or even exceed the cost of the canister of fluid to the consumer.

Another concern associated with the mechanical pressure regulators currently in use is that they incur high costs relative to other components of the fluid pressure control device and chemical analyzer. Often this one component is the single most expensive component of the fluid pressure control device and the chemical analyzer.

Yet a further drawback of mechanical pressure regulators is that they require periodic purging because of $CO_2$ diffusion through the various seals and diaphragms of the mechanical pressure regulator. This problem is compounded over longer periods of operation. Thus, because of the periodic purging, a significant portion of the gas stored in the canister of fluid is simply wasted to ensure that the calibration gas used in calibration is comprised of the appropriate proportions of $CO_2$ and other gases. Moreover, in order to function properly mechanical pressure regulators require a minimum pressure in the pressurized fluid canister. Once the pressure in the canister drops below the threshold pressure, typically about 25 psi, the remaining volume of gas in the canister of fluid is simply wasted.

Accordingly, it is desirable to provide a fluid pressure control device to supply calibration gases to a chemical analyzer that employs a relatively low-pressure canister of fluid and avoids the need for a mechanical pressure regulator, thereby avoiding the waste, high costs, and maintenance associated with current systems.

SUMMARY

One aspect of the present disclosure is directed to a fluid pressure control device, including a pressurized fluid inlet, a first valve in fluid communication with the pressurized fluid inlet and controlling the flow of fluid from the pressurized fluid inlet, a first pressure measurement device detecting a fluid pressure downstream of the first valve, and a controller electrically coupled to the first valve. The first pressure measurement device causes the controller to operate the first valve such that a fluid downstream of the first valve is maintained at a substantially constant pressure.

The controller of the fluid pressure control device may include a processor. The fluid pressure control device may include an analyzer downstream of the first valve in selective fluid communication with the pressurized fluid inlet. Additionally, a second valve may be disposed between the first valve and the analyzer. The analyzer may be a blood gas analyzer. In at least one aspect of the disclosure the first pressure measurement device detects a change in fluid pressure between the first valve and the analyzer.

The fluid pressure control device may include a second pressure measurement device is disposed upstream of the first valve and senses a fluid pressure upstream of the first valve. According to one aspect of the disclosure, when the fluid pressure sensed by the second pressure measurement device is greater than a threshold, the first valve opens for a specified time period. According to another aspect of the disclosure when the fluid pressure sensed by the second pressure measurement device is less than a threshold, the first valve opens until a sensed fluid pressure at the first pressure measurement device exceeds a second threshold.

The fluid pressure control device may include an orifice having an internal diameter, the internal diameter of the orifice different than at least a portion of the internal diameter of a lumen fluidly connecting the first valve and the analyzer.

The pressurized fluid inlet of the pressure control device may connect to a canister of fluid, the canister of fluid being separable from the device. The canister may include a diaphragm, the diaphragm configured to be punctured by a pin having a bore therethrough, at least a portion of the bore forming the pressurized fluid inlet.

The first valve of the pressure control device may be a two-way valve, and the second valve may be a three-way valve. The fluid may be a gas.

Yet a further aspect of the present disclosure is directed to a gas analyzer system, including a pressurized calibration gas canister, a two-way valve having an inlet and an outlet, the pressurized calibration gas canister in fluid communication with the inlet of the two-way valve. The gas analyzer system also includes a three-way valve having a calibration gas inlet, an atmospheric gas inlet, and a common outlet, the two-way and three-way valves being in fluid communication. A lumen fluidly connects the two-way valve and the three-way valve. The gas analyzer system also includes a first pressure measurement device detecting calibration gas pressure downstream of the two-way valve, an electronic controller coupled to the first pressure measurement device and controlling the two-way valve such that calibration gas in the lumen is maintained at a substantially constant pressure, and a gas analysis unit in fluid communication with the common outlet of the three-way valve. The gas analyzer system may include an orifice in the lumen.

According to one aspect of the disclosure, when the first pressure measurement device detects a pressure drop below a first threshold pressure, the electronic controller opens the two-way valve.

In addition, the gas analyzer system may include a second pressure measurement device, the second pressure measurement device coupled to the electronic controller and detecting calibration gas pressure upstream of the two-way valve. According to one aspect of the disclosure when the detected pressure upstream of the two-way valve is greater than about 17 psi, the two-way valve to opens for a pre-set period. According to a further aspect of the disclosure, when the detected pressure upstream of the two-way valve is between about 5 psi and 10 psi, the two-way valve opens until a pressure detected by the first pressure measurement device exceeds a second threshold pressure.

Yet a further aspect of the present disclosure is directed to a method for controlling fluid pressure of a fluid supplied to an analyzer. The method includes connecting a pressurized fluid source vessel to a fluid pressure control device including a two-way valve and a three-way valve, selectively switching the three-way valve such that the three-way valve provides atmospheric gas or fluid from the pressurized fluid source vessel to an analyzer in fluid communication with the three-way valve, sensing the pressure of fluid from the pressurized fluid source vessel at a location between the three-way valve and a two-way valve, and selectively opening the two-way valve upon detection of a fluid pressure less than a first threshold such that the sensed fluid pressure remains substantially constant and at a pressure lower than the pressurized fluid source vessel. Additionally the sensed fluid pressure may be maintained within a range of about 2 psi to about 5 psi.

Further, the method may include sensing a pressure of the fluid in the pressurized fluid source vessel. Additionally, upon detection of a pressure of fluid in the pressurized fluid source vessel in excess of a second threshold, the period that the two-way valve is opened is set to a fixed time period. Alternatively or in addition, upon detection of a pressure of fluid in the pressurized fluid source vessel less than a second threshold, the two-way valve may be opened until the sensed pressure at the location between the three-way valve and the two-way valve exceeds a third threshold. The fluid from the pressurized fluid source vessel may be a gas.

BRIEF DESCRIPTION OF THE DRAWINGS

Various aspects of the present disclosure are described herein with reference to the drawings, wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail. Those skilled in the art will understand that the embodiments according to the present disclosure may be configured for use with either liquids or gases.

Figure 1:
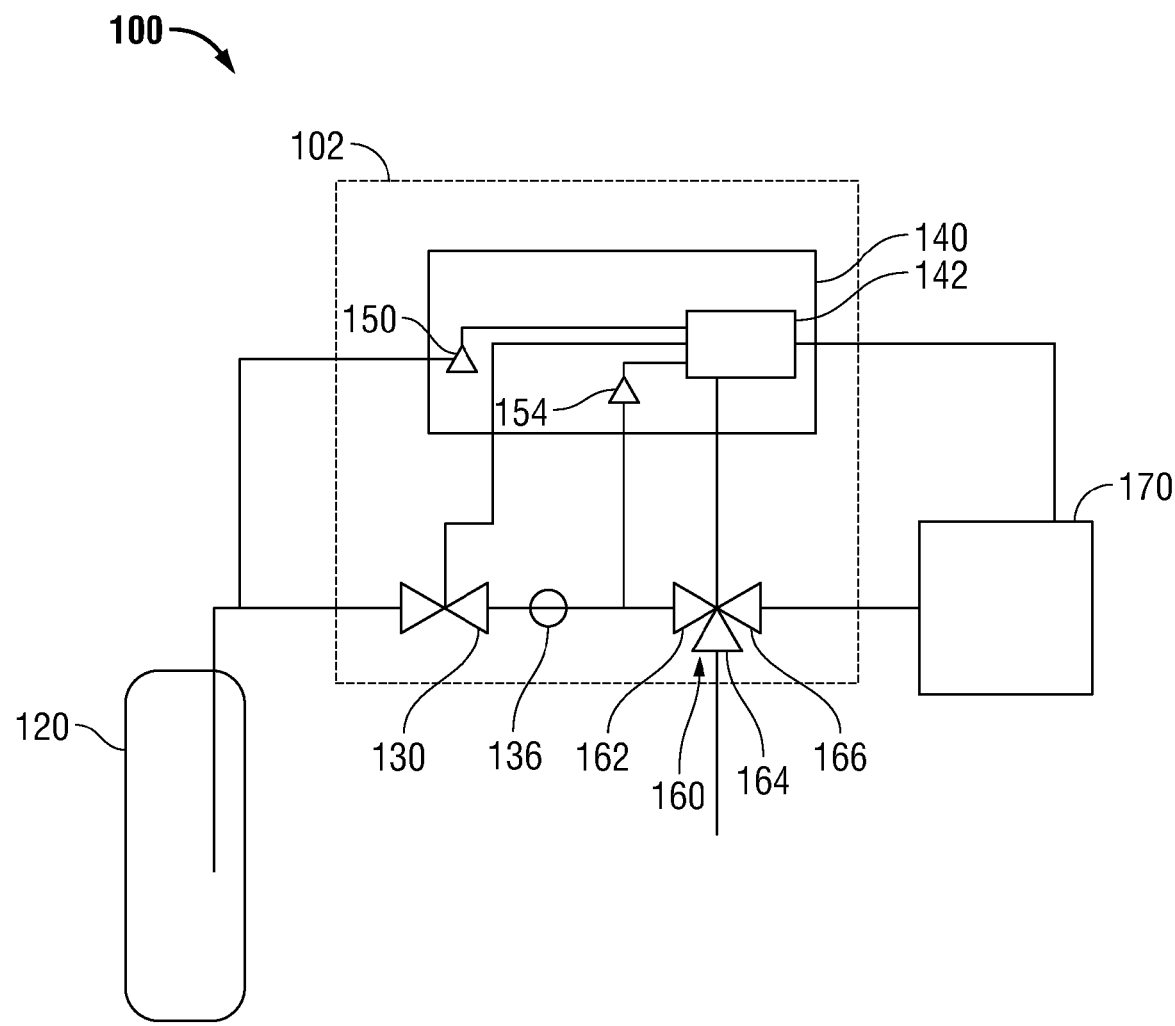
FIG. 1 is a schematic of a gas analyzer system according to the present disclosure.

FIG. 1 depicts a schematic representative of a gas analyzer system 100 including a fluid pressure control device 102. Components of the fluid pressure control device 102 are shown and will be discussed in greater detail below. Gas analyzer system 100 includes pressurized fluid supply 120, which contains pressurized fluid. Pressurized fluids may be any type of fluids, such as liquids or gases, i.e., calibration gas. Pressurized fluid supply 120 may be a pressurized fluid source vessel, such as a pressurized calibration gas canister or other canister of fluid that is separable from the fluid pressure control device 102. Pressurized fluid supply 120 is formed of a suitable material to contain pressurized fluids, such as steel, aluminum, fiberglass, carbon fiber, or a combination of these materials. In embodiments, pressurized fluid supply 120 may be a gas line or other supply system. Pressurized fluid supply 120 typically contains a mixture of Nitrogen ($N_2$), Oxygen ($O_2$), and Carbon dioxide ($CO_2$), though the use of other pressurized fluids is contemplated. Disposed downstream of the pressurized source vessel 120 is a high-pressure (HP) pressure measurement device 150. The HP pressure measurement device 150 senses the pressure of the pressurized fluid in the pressurized fluid supply 120. More accurately, as shown in FIG. 1 the HP pressure measurement device 150 measures the pressure of the pressurized fluid at a point between the pressurized fluid's exit through the pressurized fluid supply 120 and a first valve 130. Alternatively, the HP pressure measurement device 150 may directly sense the pressure in the pressurized fluid supply 120. The detection of the pressure of the pressurized fluid in the pressurized fluid supply 120 is used in certain embodiments of the present disclosure to set a control algorithm, though in certain embodiments the HP pressure measurement device 150 may be excluded from the gas analyzer system 100 entirely.

Downstream from the HP pressure measurement device 150 is a first valve 130. The first valve 130 is a fast-switching valve that controls the flow of pressurized fluid from the pressurized fluid supply 120 to the gas analyzer system 100. In an open position, first valve 130 fluidly connects the pressurized fluid supply 120 allowing pressurized fluid to flow from the pressurized fluid supply 120, and in a closed position isolates the pressurized fluid supply 120. The first valve 130 may be a two-way valve having an inlet and an outlet, and as shown in FIG. 1, the pressurized fluid supply 120 is in fluid communication with the inlet of the two-way valve. First valve 130 may be electromechanically operated using for example, a solenoid. First valve 130 may be a direct operated solenoid valve, such as a Series S070 3 Port Solenoid Valve (available from SMC® Corporation of America). The first valve 130 may be any suitable flow control device configured to control the flow of pressurized fluids downstream of the pressurized fluid supply 120. Disposed downstream of the first valve 130 is a low-pressure (LP) pressure measurement device 154. An LP pressure measurement device 154 senses or detects a fluid pressure of the pressurized fluid between the first valve 130 and a second valve 160, as will be discussed further below. The first valve 130 can be actuated in response to the pressure detected by the LP pressure measurement device 154. By quickly opening and closing the first valve 130, a small volume of pressurized fluid is allowed to pass the first valve 130. In this fashion, the pressure detected by the LP pressure measurement device 154 can be maintained within a narrow range, and the fast acting first valve 130 effectively operates as a pressure reducing valve for the gas analyzer system 100. The operation of the first valve 130 is controlled by a controller 140, as will be discussed in greater detail below.

HP pressure measurement device 150 and LP pressure measurement device 154 may be a surface-mounted package such as an NPP-301 Series Surface Mount Pressure Sensor (available from General Electric Company). The pressure measurement devices 150, 154 may incorporate transducers or any other suitable pressure sensor.

An orifice 136 is disposed between the first valve 130 and the LP pressure measurement device 154. Orifice 136 is a device or region of a lumen 119 (FIG. 3) having a reduced internal diameter that is configured to reduce pressure spikes within the flow control apparatus 102 caused by the opening of the first valve 130. The maximum flow of pressurized fluid is limited by the orifice 136, such that the LP pressure measurement device 154 measures the pressure of pressurized fluid flowing through the fluid pressure control device 102 without significant fluctuations. In embodiments, the orifice 136 may be a ⅛-inch diameter 5000-Series metal flow restrictor (available from Mott Corporation), though any suitable flow restrictor or flow jet may be used.

As shown in FIG. 1, the second valve 160 is disposed downstream of the LP pressure measurement device 154. The second valve 160 may be configured to operate similarly to first valve 130, discussed above, in that it may be solenoid operated. As depicted in FIG. 1, second valve 160 is a three-way valve that has a normally closed calibration gas inlet 162 in fluid communication with the pressurized fluid supply 120, a normally open atmospheric gas inlet 164 in fluid communication with atmosphere, and a common outlet 166 in fluid communication with an analyzer 170. By selectively switching which ports of the second valve 160 are connected, the second valve 160 can provide either atmospheric gas or pressurized fluid from the pressurized fluid supply 120 to the analyzer 170, which is in fluid communication with the common outlet 166.

Analyzer 170 is configured to analyze the composition of fluids. Analyzer 170 may be any type of chemical analyzer, such as a gas analysis unit or more particularly, a blood gas analyzer. Analyzer 170 is coupled to the fluid pressure control device 102 and is electrically coupled to a controller 140. According to one embodiment, the analyzer 170 sends a signal to the controller 140 when it requires an input of pressurized fluid, and the controller 140 controls the second valve 160 to allow flow of low-pressure pressurized fluid to the analyzer 170. Analyzer 170 may incorporate a pump downstream of the second valve 160 to drive pressurized fluid through analyzer 170.

Figure 2:
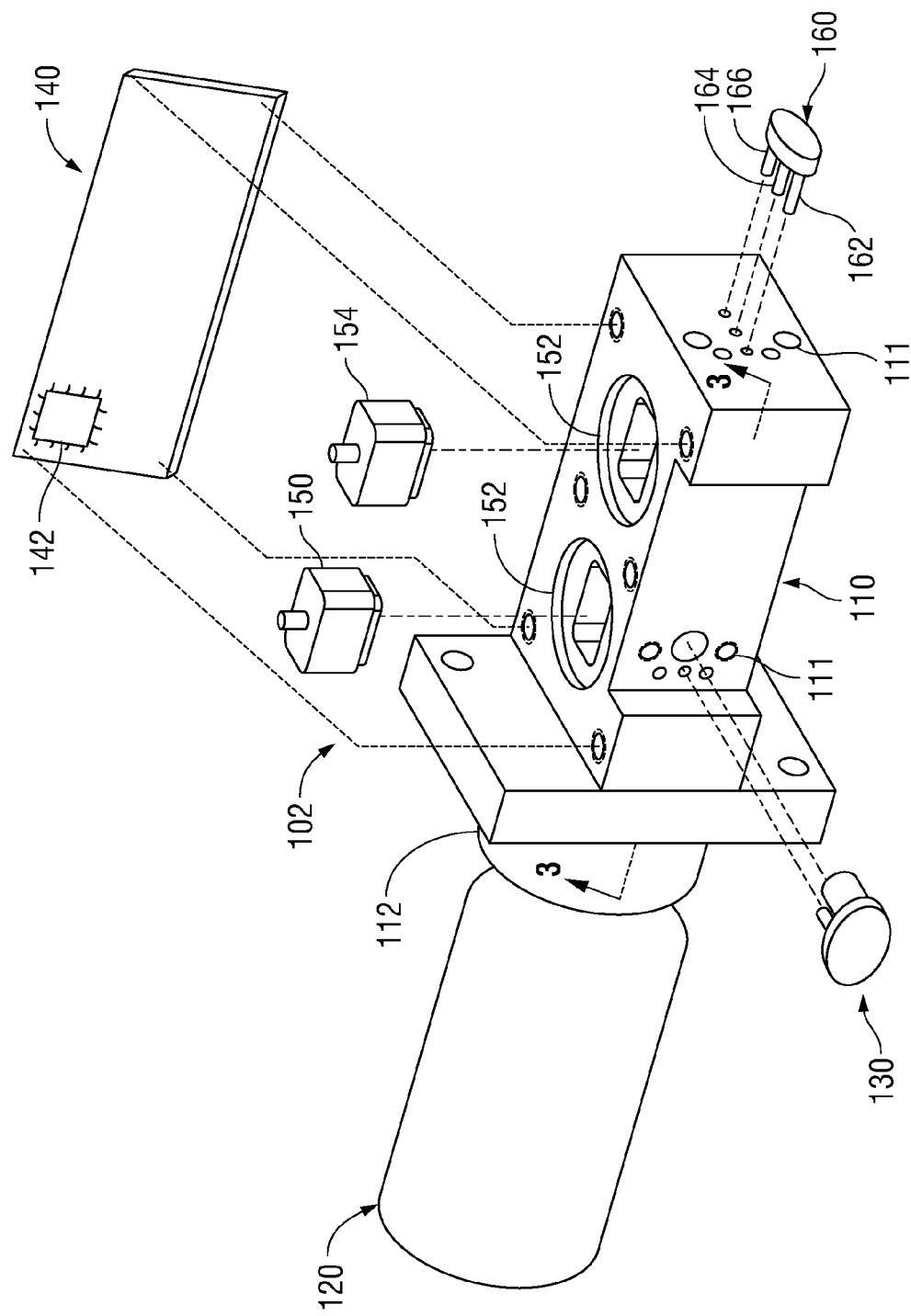
FIG. 2 is a perspective view of a fluid pressure control device according to one aspect of the present disclosure.
Figure 3:
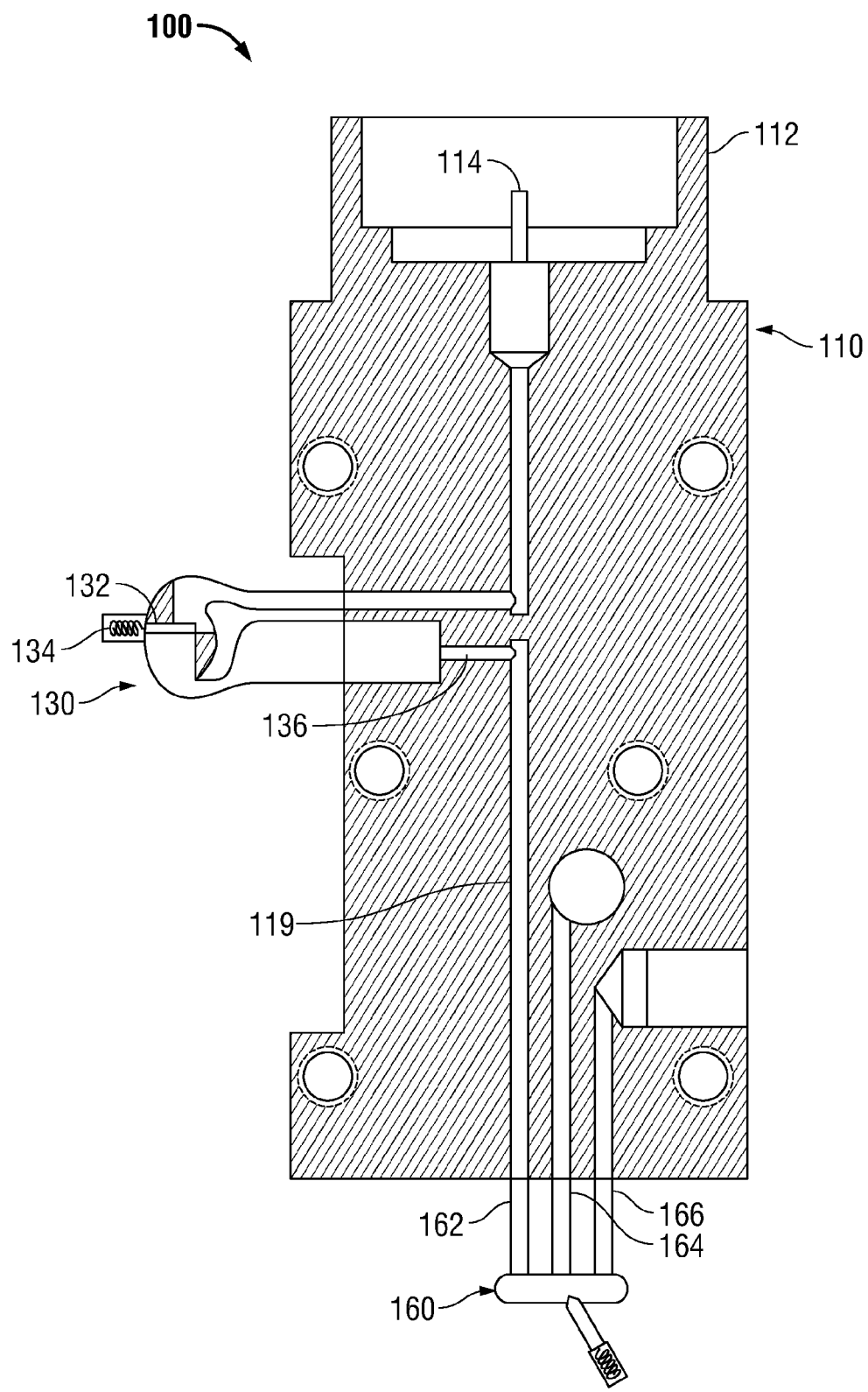
FIG. 3 is a cross-sectional view taken along section line 3-3 of the fluid pressure control device and pressurized fluid supply of FIG. 2.

In the embodiment depicted in FIGS. 2 and 3, the above-described fluid pressure control device 102 is disposed within a housing 110. Housing 110 is a manifold containing components of the fluid pressure control device 102, and may be formed of aluminum, brass, steel, or other suitable materials. Housing 110 is configured for releasable connection to various components of the fluid pressure control device 102. First valve 130 and second valve 160 may be press-fit, threaded, locked, or otherwise coupled to housing 110. First valve 130 and second valve 160 may also incorporate guide pins (not shown) that align with guide bores 111 located in housing 110, to ensure proper alignment. Further, HP pressure measurement device 150 and LP pressure measurement device 154 may be press-fit, threaded, locked, or otherwise coupled to ports 152 in housing 110.

Fluid pressure control device 102 receives pressurized fluid supply 120 through pressurized fluid supply receiver 112. Pressurized fluid supply 120 may be attached to the pressurized fluid supply receiver 112 of the housing 110 by a threaded connection. Alternatively, a bayonet-type coupling or a clamp may be utilized.

Figure 4:
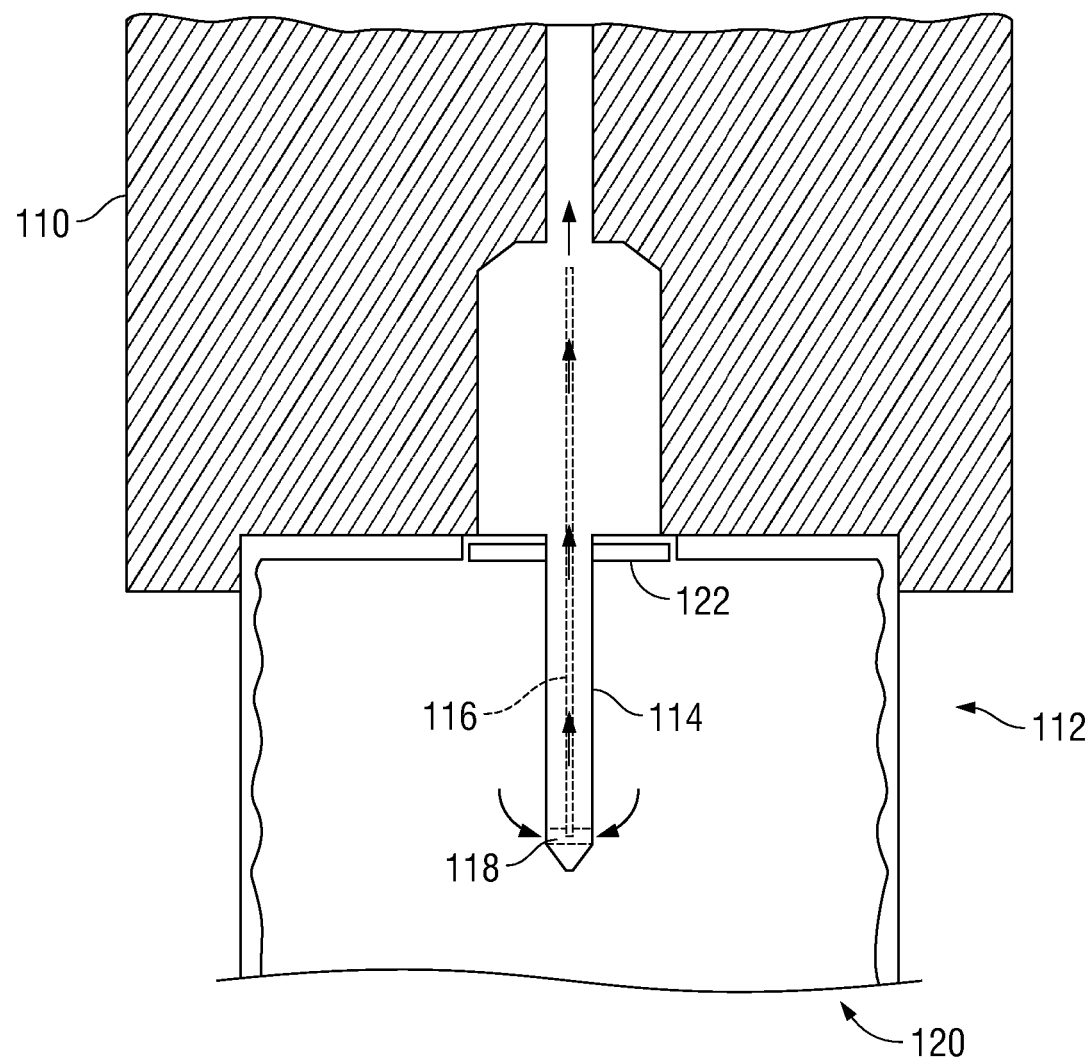
FIG. 4 is an enlarged cross sectional view of a pressurized fluid supply interconnected with the fluid pressure control device as shown in FIG. 2.

Turning to FIG. 4, the engaged pressurized fluid supply receiver 112 and pressurized fluid supply 120 are shown in cross-section. Pressurized fluid supply 120 has a diaphragm 122 that is configured to be punctured by a pin 114 mounted in the pressurized fluid supply receiver 112 and having a bore 116 therethrough. Pin 114 may be press-fit, threaded, or otherwise engaged within pressurized fluid supply receiver 112. The pin 114 also has a cross-bore 118 or other pressurized fluid inlet near the tip, and allows pressurized fluid from the pressurized fluid supply 120 to enter the cross-bore 118, and migrate through bore 116 and into housing 110. Pin 114 may be tapered or blunt, and is configured to sealably penetrate diaphragm 122 of pressurized fluid supply 120. In embodiments, diaphragm 122 may be a sealed disc or other sealing structure engaged with pressurized fluid supply 120.

As noted above, first valve 130 and second valve 160 may be electromagnetically or solenoid operated. Specifically, as shown with respect to FIG. 3, the first valve 130 may employ a solenoid pin 132 that is translated through an interior portion of first valve 130 by magnetic forces generated by an electromagnetic coil 134. The translation of solenoid pin 132 selectively opens or closes the first valve 130 by allowing or inhibiting the passage of pressurized fluids. The pressurized fluid supply 120, the HP pressure measurement device 150, the first valve 130, the LP pressure measurement device 154, the second valve 160, and the analyzer 170 are selectably in fluid communication and are interconnected by a series of lumens 119 formed in the housing 110 as shown, for example, in FIG. 3. The lumens 119 may have any desirable geometry or configuration to transport pressurized fluids from the pressurized fluid supply 120 to the analyzer 170.

As noted above, the fluid pressure control device 102 includes a controller 140 that is electrically coupled to the first valve 130, the second valve 160, and the analyzer 170. Controller 140 is also coupled to the LP pressure measurement device 154, and controls the first valve 130 such that a pressure of the pressurized fluid in the lumen 119 between the first valve 130 and the second valve 160 remains substantially constant. Controller 140 is programmed with one or more software algorithms that govern the operation of fluid pressure control device 102. In embodiments, controller 140 includes a processor 142 to implement the software algorithms. The software algorithms may be stored in on-board memory on the processor 142 or on a separate memory e.g., an EEPROM or the like (not shown). Controller 140 may be configured to be mounted to the housing 110 of the fluid pressure control device 102, as shown, or may be separate from the fluid pressure control device 102.

As described above, controller 140 includes one or more algorithms that dictate the manner in which the first valve 130 opens and closes. In one embodiment, the algorithms are implemented based on the detected pressure of the pressurized fluid source 120. Generally, the algorithms of the controller cause the first valve 130 to open for a longer period of time when the pressure detected by HP pressure measurement device 150 is lower. Thus, the algorithms take into account the higher velocities and mass flow rates inherent in higher pressure fluid flows and adjusts the performance of the first valve 130 accordingly.

The LP pressure measurement device 154 causes the controller 140 to operate and selectively open the first valve 130 upon detection of a pressurized fluid having a pressure less than a threshold pressure (e.g., about 1 psi). By repeated operation of the first valve 130, the pressure of pressurized fluid downstream of the first valve 130 (i.e., between the first valve 130 and the second valve 160), can be maintained at a substantially constant pressure and at a pressure lower than pressurized fluid within the pressurized fluid supply 120. For example, the sensed or detected pressure of the pressurized fluid may be maintained within a range of about 1 psi to about 5 psi. Alternatively, the pressurized fluid may be maintained within another pressure range, such as between about 2 psi to about 5 psi, or between about 2 psi and about 3 psi. Those skilled in the art will appreciate that other pressure ranges may be employed without departing from the scope of the present disclosure.

Specifically, upon sensing or detecting a pressure below a threshold (e.g., about 2 psi), a signal is sent by controller 140 to open first valve 130. As noted above, the time period the first valve 130 will remain open may be based on the pressure of the pressurized fluid in the pressurized fluid supply 120. Typically, the pressure in the pressurized fluid supply 120 is sensed or detected by the HP pressure measurement device 150 prior to operation of the first valve 130. When the sensed or detected pressure upstream of the first valve 130, i.e., the pressurized fluid supply 120, has an initial pressure above a high pressure threshold value (e.g., about 17 psi), the first valve 130 opens for a pre-set period, for example, a fixed 3 ms opening cycle. If the sensed or detected pressure upstream of the first valve 130 is between a low pressure threshold and the high pressure threshold (e.g., between about 10 psi and about 17 psi), first valve 130 may open for a different fixed time period. In particular, where the sensed or detected pressure of the pressurized fluid supply 120 is between about 13 psi and about 17 psi, the first valve 130 may open in a fixed 4 ms cycle. Further, where a sensed or detected pressure of the pressurized fluid supply 120 is between about 10 psi and about 13 psi, the first valve 130 may open in a fixed 5 ms cycle.

Finally, if the sensed or detected pressure upstream of the first valve 130 is below the low pressure threshold value (e.g., about 10 psi), no set period of time is employed by the controller 140 for closing the first valve 130. Instead, the first valve 130 opens for a time period based on a pressure sensed or detected by the LP pressure measurement device 154. For example, when the sensed or detected pressure upstream of the first valve 130 is between about 5 psi and about 10 psi, and the pressure sensed by the LP measurement device 154 is below a threshold (e.g., 2 psi), the first valve 130 will be opened by the controller 140 and remains open until a pressure sensed or detected by the LP pressure measurement device 154 exceeds another threshold pressure (e.g., about 3 psi). One of skill in the art will recognize that different pressures and times may be used with the fluid pressure control device 102 without departing from the scope of the initial disclosure.

Figure 5:
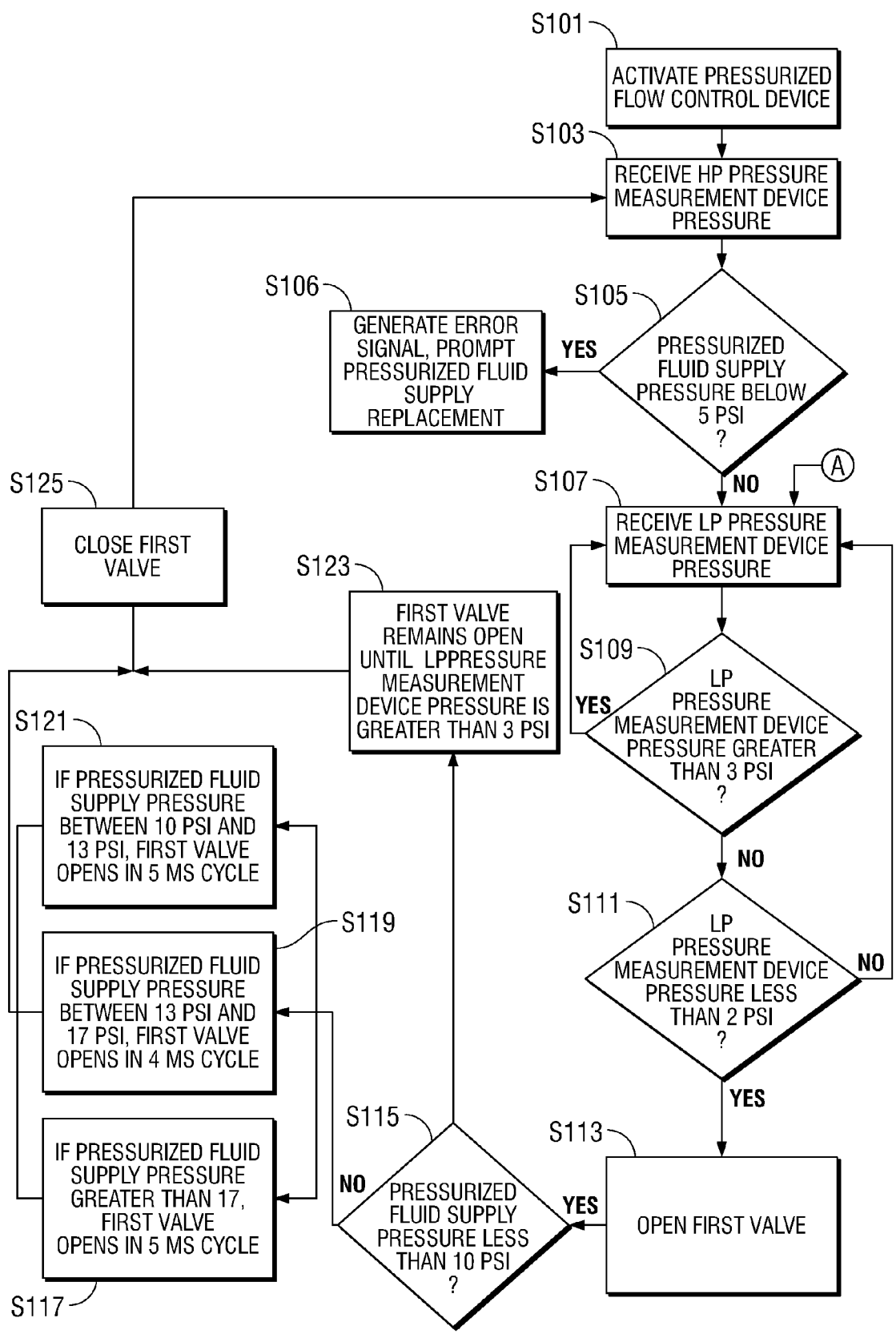
FIG. 5 is a flowchart illustrating the control process of the fluid pressure control device according to the present disclosure.

Turning to FIG. 5, a process diagram describes the method of controlling fluid pressure of a pressurized fluid supplied to the analyzer 170, from the perspective of operation of the fluid pressure control device 102 according to one embodiment of the disclosure. Pressurized fluid supply 120 is connected to the fluid pressure control device 102. Once the fluid pressure control device 102 is activated [S101], the controller 140 receives a signal from the HP pressure measurement device 150 representative of the pressure in the pressurized fluid supply 120 [S103]. If the pressurized fluid supply 120 contains pressurized fluid below about 5 psi [S105], the pressurized fluid supply 120 is incapable of providing sufficient pressurized fluid for calibration of the analyzer 170. The controller 140 generates an error signal or alarm and prompts an operator to replace the pressurized fluid supply 120 [S106].

If the pressurized fluid supply 120 has sufficiently pressurized fluid (i.e., above approximately 5 psi), the pressure at the LP pressure measurement device 154 is sensed [S107] and a representative signal is sent to the controller 140. If the pressure at the LP pressure measurement device 154 is between about 2 psi and about 3 psi [S109, S111], the pressure at the LP pressure measurement device 154 is continually monitored until the pressure at the LP pressure measurement device 154 drops below about 2 psi.

In the event that the pressure sensed by the at the LP pressure measurement device 154 drops below about 2 psi, the controller 140 signals the first valve 130 to open [S113], providing pressurized fluid at a higher pressure to the fluid pressure control device 102 from the pressurized fluid supply 120. The period of time that the first valve 130 is open is dictated by the algorithms described above, taking into account the pressure of the pressurized fluid supply 120 [S115, S117, S119, S121, S123]. Once the period that the first valve 130 is open has elapsed or the desired pressure at the LP pressure measurement device 154 has been achieved, the first valve 130 is closed [S125]. The controller 140 receives a signal representative of the pressure sensed or detected by the HP pressure measurement device 150 to determine whether the pressurized fluid supply 120 requires replacement, and the cycle repeats as long as power is supplied to the controller 140. Once the pressure sensed or detected by the LP pressure measurement device 154 drops below about 2 psi, the routine for control of the first valve 130 is initiated, as described above with reference to FIG. 5. By repeating the steps outlined in FIG. 5, the pressure sensed or detected by the LP pressure measurement device 154 can be maintained substantially constant, and at a pressure lower than that of the pressurized fluid supply 120.

Figure 6:
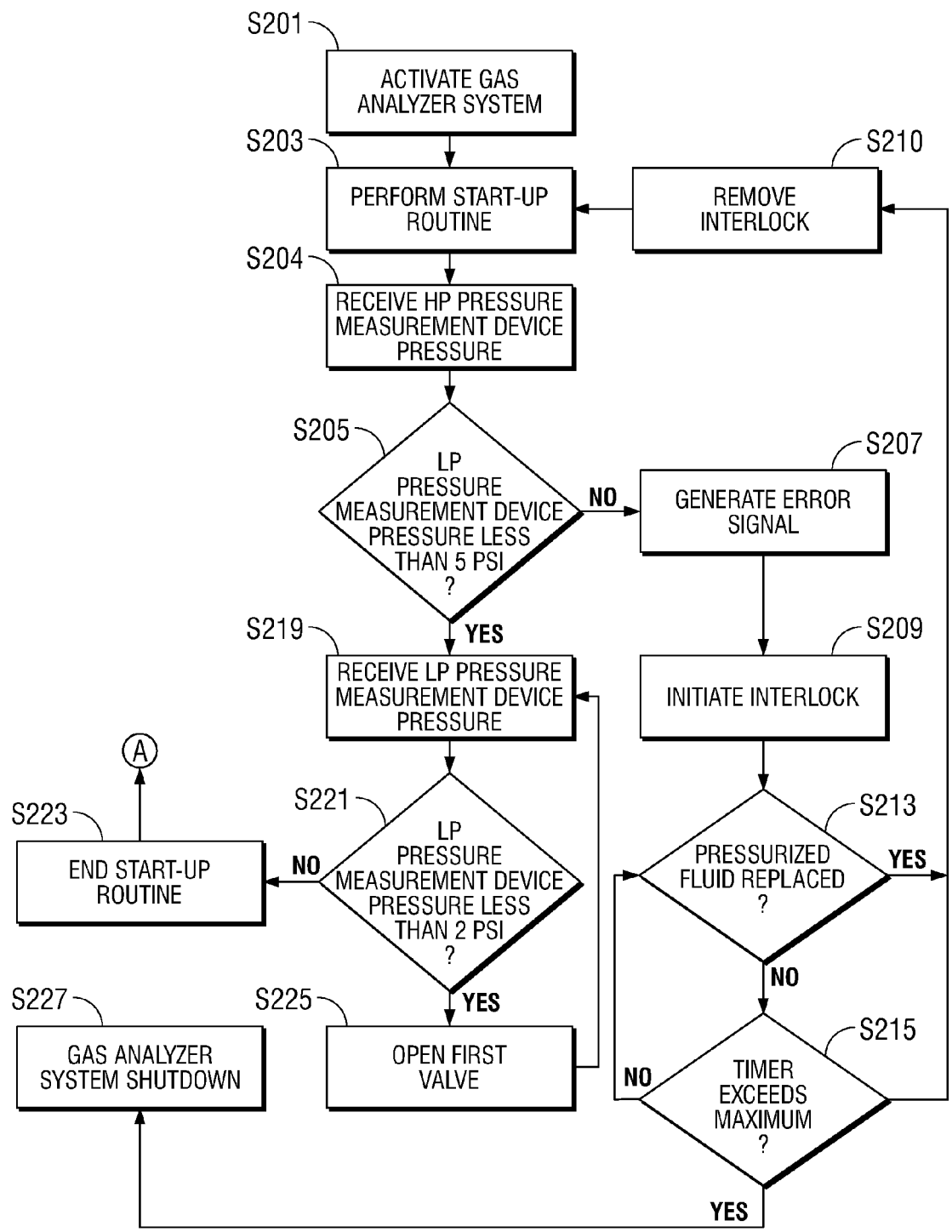
FIG. 6 is a flowchart illustrating the control process of a gas analyzer system according to the present disclosure.

Turning to FIG. 6, the operation of the gas analyzer system 100 employing a fluid pressure control device 102 of the present disclosure is described. As the analyzer system 100 is activated [S201], a signal is sent to the controller 140 to perform a start-up routine [S203]. As part of the start-up routine controller 140 receives a pressure reading from HP pressure measurement device 150 [S204]. If the pressurized fluid supply 120 has been depleted, an alarm may indicate the status to the user [S205, S207]. In some embodiments this may result in the immediate shutting down of the gas analyzer system 100. Alternatively, and as depicted in FIG. 6, a device interlock may be initiated [S209] after generation of the error signal [S207]. The device interlock prevents the analyzer 170 from being calibrated or having its calibration cycle run when there is insufficient pressurized fluid in the pressurized fluid supply 120.

In some embodiments, the gas analyzer system 100 may remain powered and wait a period of time [S215] for replacement of the pressurized fluid supply 120 [S213]. If the pressurized fluid supply 120 is not replaced within the maximum time period the gas analyzer system 100 shuts off [S227]. However, if prior to exceeding the maximum time since the interlock was initiated [S209] the pressurized fluid supply 120 is replaced [S213] the error signal will be cleared, the device interlock is removed [S210], and the start-up routine [S203] is re-initiated.

If when sensed the HP pressure measurement device 150 pressure is above 5 psi, indicating that calibration is possible [S205], then the pressure at the LP pressure measurement device 154 is sensed or detected [S219]. If the detected LP pressure measurement device 154 is above about 2 psi, this indicates that the analyzer 170 is ready for operation and pressurized fluid is sufficiently pressurized and available for use. In FIG. 6, the startup routine is ended [S223] and operation of the fluid pressure control device 102 continues as described above with respect to FIG. 5, starting at reference A. If, however, the sensed pressure at the LP pressure measurement device 154 is below about 2 psi, for example indicating a recent change of the pressurized fluid supply 120, one or more 3 ms pulses of the first valve 130 [S225] may be employed to quickly bring the pressure sensed or detected by the LP pressure measurement device 154 [S219] above the threshold pressure (e.g., about 2 psi). Once the threshold pressure has been achieved [S221], the start-up routine is ended and operation of the fluid pressure control device 102 continues as described above with respect to FIG. 5.

A pump (not shown) is disposed in the analyzer 170, and is fluidly coupled to the common outlet 166 of the second valve 160. As noted above, in a normally open position, the common outlet 166 of the second valve 160 is connected to the normally open atmospheric inlet 164 of the second valve 160, which is open to the atmosphere. Upon receiving a request for pressurized fluid from the analyzer 170, the controller 140 will switch the second valve 160 from its normally open position, where the pump is connected to the atmosphere, to a position connecting the calibration gas inlet 162 to the pump. To achieve this connection, the second valve 160 will be switched to connect the normally closed calibration gas inlet 162 with the common outlet 166. The second valve 160 may be maintained in this position until a signal is sent from the analyzer 170 either requesting atmospheric gas, indicating that sufficient time has elapsed for the calibration process, or that sufficient volume or mass of pressurized fluid has passed through the analyzer 170 and the second valve 160 may be switched to the normally open position.

As will be appreciated by those of skill in the art, the volume of pressurized fluid that must flow through the analyzer 170 is more than required for calibration due to the fact that some volume of the pressurized fluid is used to purge the gas analyzer system 100 and ensure that no residual atmospheric gas is mixed with the calibration gas in the calibration process.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

The invention claimed is:

1. A fluid pressure control device, comprising:
 a pressurized fluid inlet;
 a first valve in fluid communication with the pressurized fluid inlet and controlling the flow of fluid from the pressurized fluid inlet;
 a first pressure measurement device detecting a fluid pressure downstream of the first valve;
 a controller electrically coupled to the first valve; and
 a second pressure measurement device disposed upstream of the first valve that senses a fluid pressure upstream of the first valve,
 wherein the first pressure measurement device causes the controller to operate the first valve such that fluid downstream of the first valve is maintained at a substantially constant pressure, and
 wherein, when the fluid pressure sensed by the second pressure measurement device is greater than a threshold, the first valve opens for a specified time period.

2. The device of claim 1, further comprising an analyzer downstream of the first valve and in selective fluid communication with the pressurized fluid inlet.

3. The device of claim 2, wherein a second valve is disposed between the first valve and the analyzer.

4. The device of claim 3, wherein the second valve is a three-way valve.

5. The device of claim 2, wherein the first pressure measurement device detects a change in fluid pressure between the first valve and the analyzer.

6. The device of claim 2, further comprising an orifice having an internal diameter, the internal diameter of the orifice different than at least a portion of the internal diameter of a lumen fluidly connecting the first valve and the analyzer.

7. The device of claim 2, wherein the analyzer is a blood gas analyzer.

8. The device of claim 1, wherein when the fluid pressure sensed by the second pressure measurement device is less than a threshold, the first valve opens until a sensed fluid pressure at the first pressure measurement device exceeds a second threshold.

9. The device of claim 1, wherein the controller includes a processor.

10. The device of claim 1, wherein the pressurized fluid inlet connects to a canister of fluid, the canister of fluid being separable from the device.

11. The device of claim 10, wherein the canister has a diaphragm, the diaphragm configured to be punctured by a pin having a bore therethrough, at least a portion of the bore forming the pressurized fluid inlet.

12. The device of claim 1, wherein the first valve is a two-way valve.

13. The device of claim 1, wherein the fluid is a gas.

14. A gas analyzer system, comprising:
 a pressurized calibration gas canister;
 a two-way valve having an inlet and an outlet, the pressurized calibration gas canister in fluid communication with the inlet of the two-way valve;
 a three-way valve having a calibration gas inlet, an atmospheric gas inlet, and a common outlet, the two-way and three-way valves being in fluid communication;
 a lumen fluidly connecting the two-way valve and the three-way valve;
 a first pressure measurement device detecting calibration gas pressure downstream of the two-way valve;

an electronic controller coupled to the first pressure measurement device and controlling the two-way valve such that calibration gas in the lumen is maintained at a substantially constant pressure; and a gas analysis unit in fluid communication with the common outlet of the three-way valve.

15. The gas analyzer system of claim 14, wherein when the first pressure measurement device detects a pressure drop below a first threshold pressure, the electronic controller opens the two-way valve.

16. The gas analyzer system of claim 14, further comprising a second pressure measurement device, the second pressure measurement device coupled to the electronic controller and detecting calibration gas pressure upstream of the two-way valve.

17. The gas analyzer system of claim 16, wherein when the detected pressure upstream of the two-way valve is greater than about 17 psi, the two-way valve to opens for a pre-set period.

18. The gas analyzer system of claim 16, wherein when the detected pressure upstream of the two-way valve is between about 5 psi and 10 psi, the two-way valve opens until a pressure detected by the first pressure measurement device exceeds a second threshold pressure.

19. The gas analyzer system of claim 14, further comprising an orifice in the lumen.

20. A method for controlling fluid pressure of a fluid supplied to an analyzer, comprising:

connecting a pressurized fluid source vessel to a fluid pressure control device including a two-way valve and a three-way valve;

selectively switching the three-way valve such that the three-way valve provides atmospheric gas or fluid from the pressurized fluid source vessel to an analyzer in fluid communication with the three-way valve;

sensing the pressure of fluid from the pressurized fluid source vessel at a location between the three-way valve and the two-way valve; and selectively opening the two-way valve upon detection of a fluid pressure less than a first threshold such that the sensed fluid pressure remains substantially constant and at a pressure lower than the pressurized fluid source vessel.

21. The method of claim 20, wherein the sensed fluid pressure is maintained within a range of about 2 psi to about 5 psi.

22. The method of claim 20, further comprising sensing a pressure of the fluid in the pressurized fluid source vessel.

23. The method of claim 22, wherein upon detection of a pressure of fluid in the pressurized fluid source vessel in excess of a second threshold, the period that the two-way valve is opened is set to a fixed time period.

24. The method of claim 22, wherein upon detection of a pressure of fluid in the pressurized fluid source vessel less than a second threshold, the two-way valve is opened until the sensed pressure at the location between the three-way valve and the two-way valve exceeds a third threshold.

25. The method of claim 20, wherein the fluid from the pressurized fluid source vessel is a gas.

26. A fluid pressure control device, comprising:

a pressurized fluid inlet;

a first valve in fluid communication with the pressurized fluid inlet and controlling the flow of fluid from the pressurized fluid inlet;

a first pressure measurement device detecting a fluid pressure downstream of the first valve;

a controller electrically coupled to the first valve; and a second pressure measurement device disposed upstream of the first valve that senses a fluid pressure upstream of the first valve, wherein the first pressure measurement device causes the controller to operate the first valve such that fluid downstream of the first valve is maintained at a substantially constant pressure, and wherein, when the fluid pressure sensed by the second pressure measurement device is less than a threshold, the first valve opens until a sensed fluid pressure at the first pressure measurement device exceeds a second threshold.

* * * * *